United States Patent [19]

Yanai et al.

[11] Patent Number: 5,422,363
[45] Date of Patent: Jun. 6, 1995

[54] STABLE PHARMACEUTICAL COMPOSITION OF FUMAGILLOL DERIVATIVES

[75] Inventors: Shigeo Yanai, Ikeda; Kazuhiro Saito; Hiroaki Okada, both of Suita, all of Japan

[73] Assignee: Takeda Chemical Industries, Inc., Osaka, Japan

[21] Appl. No.: 167,479

[22] Filed: Dec. 15, 1993

[30] Foreign Application Priority Data

Dec. 16, 1992 [JP] Japan .................................. 4-335828

[51] Int. Cl.⁶ ...................... A61K 31/00; A01N 43/00
[52] U.S. Cl. .................................................. 514/410
[58] Field of Search ............................................ 514/410

[56] References Cited

U.S. PATENT DOCUMENTS 4,886,803 12/1989 Sueda et al. ........................ 514/252

FOREIGN PATENT DOCUMENTS

325199A3  7/1989  European Pat. Off. .
354767A1  2/1990  European Pat. Off. .
354787A1  2/1990  European Pat. Off. .
357061A1  3/1990  European Pat. Off. .
359036A1  3/1990  European Pat. Off. .
386667A1  9/1990  European Pat. Off. .
387650A1  9/1990  European Pat. Off. .
415294A2  3/1991  European Pat. Off. .
461427A2  12/1991  European Pat. Off. .
470569A1  2/1992  European Pat. Off. .

OTHER PUBLICATIONS

*The Merck Index*, S. Budavari (Editor), Merck & Co., Rahway, N.J., p. 1342, monograph No. 8418, "sesame oil", and page 396, monograph No. 2528 "corn oil", (1989).

*Primary Examiner*—Werren B. Lone
*Attorney, Agent, or Firm*—David G. Conlin; David S. Resnick

[57] ABSTRACT

A pharmaceutical composition having improved stability which comprises a fumagillol derivative and a fatty acid ester of glycerin or polyglycerin is disclosed. The composition is useful for treating diseases associated with angiogenesis such as hepatoma, etc.

31 Claims, No Drawings

STABLE PHARMACEUTICAL COMPOSITION OF FUMAGILLOL DERIVATIVES

FIELD OF THE INVENTION

The present invention relates to a stable pharmaceutical composition of fumagillol derivatives which are angiogenesis inhibitory substances useful as medicaments.

BACKGROUND OF THE INVENTION

Angiogenesis is the development or growth of blood vessels. It has been found that angiogenesis is closely related to diseases such as cancer, diabetic retinopathy, rheumatoid arthritis and the like. For treating such diseases angiogenesis inhibitory substances have potential because they inhibit the development of blood vessels and thus blood supply to the site of the diseases. This novel mechanism of action is different from that of conventional anticancer agents. Since angiogenesis is essential particularly for the growth of solid neoplasm, there is great hope that angiogenesis inhibitory substances will aid the fight against cancer. As a result of screening of angiogenesis inhibitory substances, fumagillol derivatives have been found and disclosed in EP-A-359,036 (JP-A 3-7270), EP-A-357,061 (JP-A 3-7222), EP-A-354,787, EP-A-386,667 (JP-A 3-14571), EP-A-387650 (JP-A 3-7271), EP-A-415,294 (JP-A 3-279376) and the like.

EP-A-470,569 (JP-A 5-969) discloses a blood vessel-obstructing agent containing both a fumagillol derivative and a blood vessel-obstructing substance such as wax (e.g., fatty acid ester of glycerol).

OBJECTS OF THE INVENTION

The main object of the present invention is to improve stability of fumagillol derivatives having angiogenesis inhibitory activity, particularly in an aqueous solution, in order to exhibit their pharmacological activity more effectively by sustained-releasing the drug from an administered site for a long period of time.

This object as well as other objects and advantages of the present invention will become apparent to those skilled in the art from the following description.

SUMMARY OF THE INVENTION

The present invention includes a pharmaceutical composition comprising a fumagillol derivative and a fatty acid ester of glycerin or polyglycerin.

DETAILED DESCRIPTION OF THE INVENTION

Examples of the fumagillol derivative include a fumagillol derivative of the formula (I):

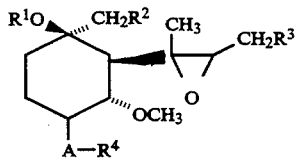

wherein $R^1$ is hydrogen; $R^2$ is halogen, $N(O)_m R^5 R^6$, $N^+ R^5 R^6 R^7 . X^-$, $S(O)_n R^5$ or $S^+ R^5 R^6 . X^-$, in which $R^5$, $R^6$ and $R^7$ represent each independently an optionally substituted hydrocarbon group or an optionally substituted heterocyclic group; $X^-$ represents a counter anion; m represents 0 or 1; n represents an integer of 0 to 2; or $R^5$ and $R^6$ together with the adjacent nitrogen or sulfur atom may form an optionally substituted nitrogen- or sulfur-containing heterocyclic group which may form a condensed ring; or $R^1$ and $R^2$ together are a chemical bond; $R^3$ is an optionally substituted 2-methyl-1-propenyl or isobutyl; A is O or $NR^8$, in which $R^8$ represents hydrogen, an optionally substituted lower alkyl group or an optionally substituted aryl group; and $R^4$ is hydrogen, an optionally substituted hydrocarbon group or an optionally substituted acyl group; or a salt thereof and the like.

In the above formula (I), halogen represented by $R^2$ includes fluorine, chlorine, bromine and iodine. When $R^1$ and $R^2$ together represent a chemical bond, an epoxy ring is formed.

The hydrocarbon group of the optionally substituted hydrocarbon group represented by $R^5$, $R^6$ or $R^7$ includes straight or branched chain $C_{1-6}$ alkyl (e.g., methyl, ethyl, propyl, isopropyl, butyl, isobutyl, sec-butyl, pentyl, isopentyl, hexyl, etc.), $C_{2-6}$ alkenyl (e.g., vinyl, allyl, 2-butenyl, methylallyl, 3-butenyl, 2-pentenyl, 4-pentenyl, 5-hexenyl, etc.), $C_{2-6}$ alkynyl (e.g., ethynyl, propargyl, 2-butyn-1-yl, 3-butyn-2-yl, 1-pentyn-3-yl, 3-pentyn-1-yl, 4-pentyn-2-yl, 3-hexyn-1-yl, etc.), $C_{3-6}$ cycloalkyl (e.g., cyclopropyl, cyclobutyl, cyclopentyl, cyclohexyl, etc.), $C_{3-6}$ cycloalkenyl (e.g., cyclobutenyl, cyclopentenyl, cyclohexenyl, cyclohexadienyl, etc.), $C_{7-13}$ aralkyl (e.g., benzyl, 1-phenethyl, 2-phenethyl, etc.), and $C_{6-10}$ aryl (e.g., phenyl, naphthyl, etc.) and the like.

The heterocyclic group of the optionally substituted heterocyclic group represented by $R^5$, $R^6$ or $R^7$ includes 5- or 6-membered heterocyclic groups containing 1 to 4 heteroatoms (e.g., nitrogen, oxygen, sulfur, etc.), for example, 2-furyl, 2-thienyl, 4-thiazolyl, 4-imidazolyl, 4-pyridyl, 1,3,4-thiadiazol-2-yl, tetrazolyl and the like. Further, the heterocyclic group may be condensed with a 5- or 6-membered ring which may contain 1 to 3 heteroatoms (e.g., nitrogen, oxygen, sulfur, etc.) other than carbon atoms (e.g., benzene, pyridine, cyclohexane, etc.) to form a condensed bicyclic group (e.g., 8-quinolyl, 8-purinyl, etc.).

The nitrogen-containing heterocyclic group which may be formed by $R^5$ and $R^6$ together with the adjacent nitrogen atom includes 4- to 7-membered nitrogen-containing heterocyclic groups which may contain 1 to 3 heteroatoms (e.g., nitrogen, oxygen, sulfur, etc.) other than a nitrogen atom (e.g., pyrrolidin-1-yl, piperidino, morpholino, piperazin-1-yl, etc.), and the like.

The sulfur-containing heterocyclic group which may be formed by $R^5$ and $R^6$ together with the adjacent sulfur atom includes 4- to 7-membered sulfur-containing heterocyclic groups which may contain 1 to 3 heteroatoms (e.g., nitrogen, oxygen, sulfur, etc.) other than a sulfur atom (e.g., tetrahydrothiophen-1-yl, 1,4-thioxan-1-yl, etc.), and the like.

The nitrogen- or sulfur-containing heterocyclic group which may be formed by $R^5$ and $R^6$ together with the adjacent nitrogen or sulfur atom may be condensed with a 5- or 6-membered ring (e.g., benzene, pyridine, pyrazine, pyrimidine, pyridazine, cyclohexane, etc.) to form a condensed bicyclic group (e.g., isoindolin-2-yl, 2-isoquinolyl, 1,3-dihydrobenzo[c]thiophen-2-yl, 2,3-dihydrobenzo[b]thiophen-1-yl, 3,4-dihydro-1H-2-benzopyran-2-yl, 3,4-dihydro-2H-1-benzopyran-1-yl, 1,2,4,5-tetrahydro-3-benzothiepin-3-yl, 1,3-dihydrothieno[ 3,4-c]pyridin-2-yl, 5,7-dihydrothieno[3,4- b]pyrazin-6-yl,5,7-dihydrothieno[3,4-d]pyridazin-6-yl, etc.) or the like.

The lower alkyl group of the optionally substituted lower alkyl group represented by $R^8$ includes straight or branched chain $C_{1-6}$ alkyl groups (e.g., methyl, ethyl, propyl, isopropyl, butyl, isobutyl, sec-butyl, pentyl, isopentyl, hexyl, etc.) and the like.

The aryl group of the optionally substituted aryl group represented by $R^8$ includes $C_{6-10}$ aryl groups (e.g., phenyl, naphthyl, etc.) and the like.

The hydrocarbon group of the optionally substituted hydrocarbon group represented by $R^4$ includes that described above with respect to that of the optionally substituted hydrocarbon represented by $R^5$, $R^6$ or $R^7$.

When the hydrocarbon group represented by $R^4$ is an alkenyl group, it preferably has no substituent.

The optionally substituted acyl group represented by $R^4$ includes residues of optionally substituted acids, for example, acyl groups derived from the corresponding acids, such as carboxylic acid acyl, sulfonic acid acyl, carbamoyl, thiocarbamoyl and sulfamoyl each of which may have at least one substituent. Examples of the optionally substituted acyl include alkanoyl, aroyl, heterocyclic carbonyl, carbamoyl, thiocarbamoyl, arylsulfonyl, alkylsulfonyl, sulfamoyl, alkoxycarbonyl, aryloxycarbonyl and the like each of which may have at least one substituent.

The alkanoyl group of the above optionally substituted alkanoyl group includes $C_{1-6}$ alkanoyl groups (e.g., formyl, acetyl, propionyl, isopropionyl, butyryl, pentanoyl, hexanoyl, etc.) and the like.

The aroyl group of the optionally substituted aroyl group includes $C_{7-11}$ aroyl groups (e.g., benzoyl, 1-naphthoyl, 2-naphthoyl, etc.) and the like.

The heterocyclic carbonyl group of the optionally substituted heterocyclic carbonyl group includes 5- or 6 membered heterocyclic carbonyl groups containing 1 to 4 heteroatoms (e.g., nitrogen, oxygen, sulfur, etc.), for example, 2-furoyl, 2-thenoyl, nicotinyl, isonicotinyl and the like.

The arylsulfonyl group of the optionally substituted arylsulfonyl group includes $C_{6-10}$ arylsulfonyl groups (e.g., benzenesulfonyl, 1-naphthylsulfonyl, 2-naphthylsulfonyl, etc.) and the like.

The alkylsulfonyl group of the optionally substituted alkylsulfonyl group includes $C_{1-6}$ alkylsulfonyl groups (e.g., methylsulfonyl, ethylsulfonyl, propylsulfonyl, butylsulfonyl, pentylsulfonyl, etc.) and the like.

The alkoxycarbonyl group of the optionally substituted alkoxycarbonyl group includes $C_{2-7}$ alkoxycarbonyl groups (e.g., methoxycarbonyl, ethoxycarbonyl, isobutoxycarbonyl, etc.) and the like.

The aryloxycarbonyl group of the optionally substituted aryloxycarbonyl group includes $C_{7-11}$ aryloxycarbonyl groups (e.g., phenoxycarbonyl, 1-naphthyloxycarbonyl, 2-naphthyloxycarbonyl, etc.) and the like.

Examples of the substituent on the optionally substituted 2-methyl-1-propenyl or isobutyl group represented by $R^3$ include hydroxyl, amino, lower ($C_{1-3}$) alkylamino (e.g., methylamino, ethylamino, isopropylamino, etc.), di-lower ($C_{1-3}$) alkylamino (e.g., dimethylamino, diethylamino) and the like. Hydroxyl and di-lower ($C_{1-3}$) alkylamino, particularly dimethylamino, are preferred.

The optionally substituted hydrocarbon group or optionally substituted heterocyclic group represented by $R^5$, $R^6$ or $R^7$; the optionally substituted nitrogen- or sulfur-containing heterocyclic group formed by $R^5$ and $R^6$ together with the adjacent nitrogen or sulfur atom which may be condensed with a further ring; the optionally substituted lower alkyl group or optionally substituted aryl group represented by $R^8$; as well as the optionally substituted hydrocarbon group and optionally substituted acyl group (e.g., alkanoyl, aroyl, heterocyclic carbonyl, carbamoyl, thiocarbamoyl, arylsulfonyl, alkylsulfonyl, sulfamoyl, alkoxycarbonyl, aryloxycarbonyl, etc.) represented by $R^4$ may contain 1 to 3 substituents at the possible positions.

Examples of such substituents include $C_{1-6}$ alkyl groups (e.g., methyl, ethyl, propyl, isopropyl, butyl, isobutyl, sec-butyl, pentyl, isopentyl, hexyl, etc.), $C_{2-6}$ alkenyl groups (e.g., vinyl, allyl, 2-butenyl, methylallyl, 3-butenyl, 2-pentenyl, 4-pentenyl, 5-hexenyl, etc.), $C_{2-6}$ alkynyl groups (e.g., ethynyl, propargyl, 2-butyn-1-yl, 3-butyn-2-yl, 1-pentyn-3-yl, 3-pentyn-1-yl, 4-pentyn-2-yl, 3-hexyn-1-yl, etc.), $C_{3-6}$ cycloalkyl groups (e.g., cyclopropyl, cyclobutyl, cyclopentyl, cyclohexyl, etc.), $C_{3-6}$ cycloalkenyl groups (e.g., cyclobutenyl, cyclopentenyl, cyclohexenyl, cyclohexadienyl, etc.), $C_{6-10}$ aryl groups (e.g., phenyl, naphthyl, etc.), amino, mono-$C_{1-6}$ alkylamino groups (e.g., methylamino, ethylamino, isopropylamino, etc.), di-$C_{1-6}$ alkylamino groups (e.g., dimethylamino, diethylamino, etc.), azido, nitro, halogen (e.g., fluorine, chlorine, bromine, iodine, etc.), hydroxyl, $C_{1-4}$ alkoxy groups (e.g., methoxy, ethoxy, etc.), $C_{6-10}$ aryloxy groups (e.g., phenoxy, naphthyloxy, etc.), $C_{1-6}$ alkylthio groups (e.g., methylthio, ethylthio, propylthio, etc.), $C_{6-10}$ arylthio groups (e.g., phenylthio, naphthylthio, etc.), cyano, carbamoyl, carboxyl, $C_{1-4}$ alkoxycarbonyl groups (e.g., methoxycarbonyl, ethoxycarbonyl, etc.), $C_{7-11}$ aryloxycarbonyl groups (e.g., phenoxycarbonyl, 1-naphthyloxycarbonyl, 2-naphthyloxycarbonyl, etc.), carboxy-$C_{1-4}$ alkoxy groups (e.g., carboxymethoxy, 2-carboxyethoxy, etc.), $C_{1-6}$ alkanoyl groups (e.g., formyl, acetyl, propionyl, isopropionyl, butyryl, pentanoyl, hexanoyl, etc.), $C_{7-11}$ aroyl groups (e.g., benzoyl, 1-naphthoyl, 2-naphthoyl, etc.), $C_{1-6}$ alkylsulfonyl groups (e.g., methylsulfonyl, ethylsulfonyl, etc.), $C_{6-10}$ arylsulfonyl groups (e.g., benzenesulfonyl, 1-naphthylsulfonyl, 2-naphthylsulfonyl, etc.), $C_{1-6}$ alkylsulfinyl groups (e.g., methylsulfinyl, ethylsulfinyl, etc.), $C_{6-10}$ arylsulfinyl groups (e.g., benzenesulfinyl, 1-naphthylsulfinyl, 2-naphthylsulfinyl, etc.), 5-or 6-membered heterocyclic groups containing 1 to 4 heteroatoms (e.g., nitrogen, oxygen, sulfur, etc.) (e.g., 2-furyl, 2-thienyl, 4-thiazolyl, 4-imidazolyl, 4-pyridyl, 1,3,4-thiadiazol-2-yl, 1-methyl-5-tetrazolyl, etc.), 5- or 6-membered heterocyclic carbonyl groups containing 1 to 4 heteroatom (e.g., nitrogen, oxygen, sulfur, etc.) (e.g., 2-furoyl, 2-thenoyl, nicotinoyl, isonicotinoyl, etc.), 5- or 6-membered heterocyclic thio groups containing 1 to 4 heteroatoms (e.g., nitrogen, oxygen, sulfur, etc.) (e.g., 4-pyridylthio, 2-pyrimidylthio, 1,3,4-thiadiazol-2-ylthio, 1-methyl-5-tetrazolylthio, etc.) and the like. Further, the heterocyclic thio group may be condensed with a benzene ring to form a condensed bicyclic thio group (e.g., 2-benzothiazolylthio, 8-quinolylthio, etc.). $C_{1-6}$ alkyl groups and $C_{1-6}$ alkanoyl groups are preferred. Furthermore, when $R^4$ represents a disubstituted carbamoyl, thiocabamoyl or sulfamoyl group, the substituents together with the nitrogen atom of the carbamoyl, thiocarbamoyl or sulfamoyl group may form a nitrogen-containing heterocyclic group (e.g., 4- to 7-membered nitrogen-containing heterocyclic groups which may contain 1 to 3 heteroatoms (e.g., nitrogen, oxygen, sulfur, etc.) other than a nitrogen atom, such as pyrrolidin-1-yl, piperidino, morpholino, piperazin-1-yl, 4-methylpiperazin-1-yl, 4-phenylpiperazin-1-yl, etc.).

The substituent in the optionally substituted hydrocarbon group or optionally substituted heterocyclic group represented by $R^5$, $R^6$ or $R^7$; the substituent in the optionally substituted nitrogen- or sulfur-containing heterocyclic group which may be formed by $R^5$ and $R^6$ together with the adjacent nitrogen or sulfur atom and may be condensed with a further ring; the substituent in the optionally substituted lower alkyl group or optionally substituted aryl group represented by $R^8$; as well as the substituent in the optionally substituted hydrocarbon group or optionally substituted acyl group (e.g., alkanoyl, aroyl, heterocyclic carbonyl, carbamoyl, thiocarbamoyl, arylsulfonyl, alkylsulfonyl, sulfamoyl, alkoxycarbonyl, aryloxycarbonyl, etc.) represented by $R^4$ may further contain 1 to 3 substituents at the possible positions.

Examples of such substituents include the aforementioned $C_{1-6}$ alkyl groups, $C_{2-6}$ alkenyl groups, $C_{2-6}$ alkynyl groups, $C_{3-6}$ cycloalkyl groups, $C_{3-6}$ cycloalkenyl groups, $C_{6-10}$ aryl groups, amino, mono-$C_{1-6}$ alkylamino groups, di-$C_{1-6}$ alkylamino groups, azido, nitro, halogen, hydroxyl, $C_{1-4}$ alkoxy groups, $C_{6-10}$ aryloxy groups, $C_{1-6}$ alkylthio groups, $C_{6-10}$ arylthio groups, cyano, carbamoyl, carboxyl, $C_{1-4}$ alkoxycarbonyl groups, $C_{7-11}$ aryloxycarbonyl groups, carboxy-$C_{1-4}$ alkoxy groups, $C_{1-6}$ alkanoyl groups, halogeno $C_{1-6}$ alkanoyl groups, $C_{7-11}$ aroyl group, $C_{1-6}$ alkylsulfonyl groups, $C_{6-10}$ arylsulfonyl groups, $C_{1-6}$ alkylsulfinyl, $C_{6-10}$ arylsulfinyl groups, 5- or 6-membered heterocyclic groups, 5- or 6-membered heterocyclic carbonyl groups, 5- or 6-membered heterocyclic thio groups and the like.

The counter anion represented by $X^-$ includes, for example, halogen ions (e.g., iodide ion, bromide ion, chloride ion, etc.), sulfate ion, phosphate ion, nitrate ion, perchlorate ion, tetrafluoroborate ion, methanesulfate ion, p-tolylsulfate ion, benzenesulfate ion, hydroxyl ion, organic carboxylate ions (e.g., oxalate ion, maleate ion, fumarate ion, succinate ion, citrate ion, lactate ion, trifluoroacetate ion, lactobionate ion, acetate ion, propionate ion, tartrate ion, ethyl succinate ion, etc.) and the like. Halogen ions are preferred.

The compound (I) has asymmetric centers in its molecule and is optically active. Its absolute configuration is based on the starting material, fumagillol. When the configuration is shown, the absolute configuration is the same as that of fumagillol. The mode of bonding of the substituents on the cyclohexane ring is as follows: . . . , ◀ and — represent α-bond, β-bond and either α- or β-bond, respectively.

In the compound (I), preferably, $R^1$ and $R^2$ together represent a chemical bond, or $R^1$ is hydrogen and $R^2$ is $N(O)_m R^5 R^6$, $N^+ R^5 R^6 R^7 . X^-$, $S(O)_n R^5$ or $S^+ R^5 R^6 . X^-$, more preferably $S^+ R^5 R^6 . X^-$. The sulfur-containing heterocyclic groups formed by $R^5$ and $R^6$ together with the adjacent sulfur atom, which may be condensed with a 5- or 6-membered ring to form a condensed bicyclic group is preferred. $X^-$ is preferably a halogen ion. The compounds wherein $R^1$ and $R^2$ together represent a chemical bond are particularly preferred.

A is preferably O or NH. O is more preferable.

$R^3$ is preferably a 2-methyl-1-propenyl or isobutyl group which is optionally substituted with hydroxyl or dialkylamino group. $R^3$ is more preferably 2-methyl-1-propenyl.

$R^4$ is preferably hydrogen or an optionally substituted carbamoyl. In particular, it is preferred when the substituent is a $C_{1-6}$ alkyl group or a $C_{1-6}$ alkanoyl group optionally substituted with halogen.

Preferred examples of the compound (I) include 6-O-(N-chloroacetylcarbamoyl)fumagillol, 6α-(N'-chloroacetylureido)-6-desoxyfumagillol, 4-(N'-chloroacetylureido)-2-(1,2-epoxy-1,5-dimethyl-4-hexenyl)-1-(1,3-dihydrobenzo[c]thiophen-2-ylio)methyl-3-methoxycyclohexanol chloride, 6-O-(N-methylcarbamoyl)fumagillol and the like.

When the compound (I) has an acidic substituent (e.g., carboxyl, etc.) or a basic substituent (e.g., amino, mono-lower alkylamino, di-lower alkylamino, nitrogen-containing heterocyclic group, etc.) in the molecule, the compound (I) may form a physiologically acceptable salt thereof. Examples of the physiologically acceptable salt include those with inorganic bases, organic bases, inorganic acids, organic acids, basic or acidic amino acids and the like. As the inorganic base which can form these salts, there are, for example, alkali metals (e.g., sodium, potassium, etc.) and alkaline earth metals (e.g., calcium, magnesium, etc.) and the like; as the organic base, there are, for example, trimethylamine, triethylamine, pyridine, picoline, N,N-dibenzylethylenediamine, ethanolamine, diethanolamine, tris(hydroxymethyl)aminomethane, dicyclohexylamine and the like; as the inorganic acid, there are, for example, hydrochloric acid, hydrobromic acid, sulfuric acid, nitric acid, phosphoric acid and the like; as the organic acid, there are, for example, formic acid, acetic acid, trifluoroacetic acid, oxalic acid, tartaric acid, fumaric acid, maleic acid, methanesulfonic acid, benzenesulfonic acid, p-toluenesulfonic acid and the like; and as the basic or acidic amino acid, there are, for example, arginine, lysine, ornithine, aspartic acid, glutamic acid and the like.

Among these salts, salts with bases (i.e., salts with inorganic bases, salts with organic bases, salts with basic amino acids) represent those formed with the carboxyl group in the substituent of the compound (I), and salts with acids (i.e., salts with inorganic acids, salts with organic acids, salts with acidic amino acids) represent those which can be formed with amino, mono-lower alkylamino groups, di-lower alkylamino groups, nitrogen-containing heterocyclic groups or the like in the substituent of the compound (I).

When the compound (I) has a di-lower alkyl amino group, a nitrogen-containing heterocyclic group or a nitrogen-containing aromatic heterocyclic group, the nitrogen atom in these groups may be further alkylated to form a quaternary ammonio group (e.g., trimethylammonio, N-methylpyridinyl, N-methylpyrrolidin-1-ylium, etc.), and the counter anion thereof includes the counter anions shown with respect to those represented by $X^-$.

The compound represented by the formula (I) or a salt thereof can be produced by using, as a starting material, fumagillol [Tarbell, D. S. et al., J. Am. Chem. Soc., 83, 3096 (1961)] which is a hydrolyzate of fumagillin produced by a microorganism. The production process as well as physical and biological properties thereof are described in detail in aforementioned EP-A 359,036, EP-A 357,061, EP-A 354,787 and the like.

The fatty acid ester of glycerin or polyglycerin in the present invention can be used as a stabilizer of the fumagillol derivatives. From the viewpoint of the stabilizing effect or sustained-releasing effect thereof on the fumagillol derivatives, saturated fatty acids having 6 to 22 carbon atoms are preferred as the fatty acid of the fatty acid esters of glycerin or polyglycerin. Examples thereof include capronic acid ($C_6$), caprylic acid ($C_8$), capric acid ($C_{10}$), lauric acid ($C_{12}$), myristic acid ($C_{14}$), palmitic acid ($C_{16}$), stearic acid ($C_{18}$), arachidic acid ($C_{20}$), behenic acid ($C_{22}$) and the like. By the term "degree of esterification" is meant the ratio of the esterified hydroxyl groups relative to the total hydroxyl groups in the fatty acid ester of glycerin or polyglycerin. The degree of esterification is preferably not less than about 60%, more preferably not less than about 80%. The degree of polymerization of the polyglycerin is preferably 2 to 16.

The fatty acid esters of glycerin or polyglycerin can be used alone or in combination of the two or more thereof. Preferably, the fatty acid esters are appropriately selected so that the degree of esterification becomes not less than about 80%.

The fatty acid esters of glycerin are preferably fatty acid triglycerides (i.e., triacylglycerol) wherein three molecules of fatty acids are attached to one molecule of glycerol through ester linkages. The fatty acids to be esterified may be the same or different and are preferably saturated fatty acids having 6 to 22 carbon atoms, more preferably saturated fatty acids having 8 to 18 carbon atoms. Among them, those having 8 to 12 carbon atoms are particularly preferred.

Some of the fatty acid triglycerides are commercially available. Examples of the commercially available fatty acid triglycerides include Miglyol 810 (caprylic acid/-capric acid triglyceride; fatty acid composition: caprylic acid=65 to 75%, capric acid=25 to 35%), Miglyol 812 (caprylic acid/capric acid triglyceride; fatty acid composition: caprylic acid=50 to 65%, capric acid =30 to 45%), Dynasan 110 (capric acid triglyceride), Dynasan 112 (lauric acid triglyceride) Dynasan 114 (myristic acid triglyceride), Dynasan 116 (palmitic acid triglyceride), Dynasan 118 (stearic acid triglyceride) and the like from Huls Aktiengesellshaft, Germany; Triester F-810 (caprylic acid/capric acid triglyceride) and the like from Nikko Chemicals, Tokyo, Japan.

These triglycerides can be used as mixtures of two or more of them.

As described above, the polyglycerin fatty acid esters of polyglycerin are preferably those wherein the polyglycerin is selected from various glycerin polymers whose degree of polymerization of glycerin is 2 to 16, more preferably 2 to 10. At least one hydroxyl group of the hydroxyl groups (the number of hydroxyl groups: the degree of polymerization+2), preferably not less than 80% of the total hydroxyl groups is acylated with fatty acids. The fatty acids are preferably saturated fatty acids. The saturated fatty acids have preferably 6 to 22 carbon atoms, more preferably 8 to 18 carbon atoms. The fatty acids to be esterified may be the same or different. Commercially available fatty acid esters of polyglycerin are various in the degree of polymerization of glycerin, kind of fatty acid and degree of esterification. Any of them can be used in the present invention.

Examples of the commercially available fatty acid esters of polyglycerin include PS-310 (tetraglycerin pentastearate), DAS-750 (decaglycerin decastearate) and the like from Sakamoto Yakuhin (Osaka, Japan); Poem J-46B (tetraglycerin hexabehenate) and the like from Riken Vitamin (Tokyo, Japan); Tetraglyn 5-S (tetraglycerin pentastearate), decaglyn 10-S (decaglycerin decastearate) and the like from Nikko Chemicals (Tokyo).

These polyglycerin fatty acid esters can be used alone or as mixtures of the two or more of them. They can also be used in combination with the fatty acid esters of glycerin.

The pharmaceutical composition of the present invention is a composition comprising a fumagillol derivative and a fatty acid ester of glycerin or polyglycerin wherein the fumagillol derivative is stabilized. The pharmaceutical composition may be in liquid or solid form. The liquid form is preferred. The pharmaceutical composition can be prepared by per se known methods, for example, by the following method.

In the case of using the fatty acid ester of glycerin or polyglycerin which is liquid at room temperature, the fumagillol derivative is added to the fatty acid ester and dissolved or dispersed in it by conventional methods such as stirring to give the desired composition.

In the case of using the fatty acid ester of glycerin or polyglycerin which is solid at room temperature, the ester is firstly converted into a liquid form. Then the fumagillol derivative is dissolved or dispersed in it, followed by solidification. This is carried out according to per se known methods. For example, the fatty acid ester of glycerin or polyglycerin is warmed to not lower than its melting point, and the fumagillol derivative is dissolved or dispersed in a liquid form of the fatty acid ester, and the resulting solution or dispersion is solidified by cooling. Solidification may be carried out, if necessary, so as to form particles or pellets by per se known methods. In the case of forming particles, for example, global microparticles having particle diameters of about 10 to about 1000 μm are preferably formed. The formation of particles can be carried out per se known methods (see, e.g., EP-A-368247). Examples of the methods include the method wherein the above solution or dispersion of the fumagillol derivative is dispersed into an aqueous phase, the spray drying method, and the spray chilling method wherein micro oil drops are formed and chilled rapidly to solidify them. In order to avoid aggregation of the particles, if necessary, an aqueous solution containing, for example, a dispersing agent (e.g., Tween 80, carboxymethyl cellulose, polyvinyl alcohol, etc.) and the like can be used for the aqueous phase.

The ratio of the fumagillol derivative in the composition based on the fatty acid esters of glycerin or polyglycerin can appropriately be selected depending upon the physicochemical properties of these components such as solubility, dispersibility and the effective dose of fumagillol derivatives. The ratio is preferably about 0.001 to about 50% (w/v), more preferably about 0.01 to about 30% (w/v).

The concentration of the fumagillol derivative in the composition can appropriately be selected depending upon the physicochemical properties of the composition. The concentration is about 0.0005 to about 30% (w/v), preferably about 0.005 to about 25% (w/v).

Additives conventionally used for preparing medicaments can be used for the composition of the present invention. Examples of the additives include those used for injectable preparations, such as preservatives (e.g., benzyl alcohol, ethyl alcohol, benzalkonium chloride, phenol, chlorobutanol, etc.), antioxidants (e.g., butylhydroxyanisole, propyl gallate, ascorbic acid palmitate, α-tocopherol, etc.), thickening agents (e.g., lecithin, hydroxypropylcellulose, aluminium stearate, etc.) and the like.

The pharmaceutical composition of the present invention is preferably obtained by per se known methods for medical use in a sterilized form.

The pharmaceutical composition of the present invention is dispersed as an emulsion or suspension by per se known methods in an aqueous suspension prepared from, for example, distilled water for injection, sodium chloride, saccharides (e.g., glucose, mannitol, inositol, etc.), dispersing agents (e.g., Tween 80 (manufactured by Atlas Powder), HCO 60 (manufactured by Nikko Chemicals), polyethylene glycol, carboxyethyl cellulose, carboxymethyl cellulose sodium, sodium alginate, etc.), etc. After the dispersion, the fumagillol derivative in a concentration effective against the disease to be treated can be administered as an injectable preparation intravenously, intraarterially, intramuscularly, subcutaneously, or into organs or foci such as tumors. When the pharmaceutical composition is in liquid form, it can directly be administered as an injectable preparation.

According to conventional methods, the pharmaceutical composition of the present invention can be molded into preparations for administration other than injection, such as external preparations (e.g., pernasal preparation, transdermal preparation, etc.), suppositories (e.g., rectal suppositories, vaginal suppositories, etc.).

To prepare external preparations, for example, the composition of the present invention can be molded into solid, semisolid or liquid nasal preparations. For the above solid preparations, the composition of the present invention is molded into powder composition as it is or after mixing it with added vehicles (e.g.,, glucose, mannitol, starch, microcrystalline cellulose, etc.), thickening agents (e.g., natural gums, cellulose derivatives, acrylic acid polymers, etc.) and the like. For the above liquid preparations, oily or aqueous suspensions are prepared according to almost the same manner as that in the above injectable preparations. As the above semisolid preparations, aqueous or oily gels or ointments are preferred. In each of these preparations, pH adjustors (e.g., carbonic acid, phosphoric acid, citric acid, hydrochloric acid, sodium hydroxide, etc.), antiseptics (e.g., p-oxybenzoic acid esters, chlorobutanol, benzalkonium chloride, etc.) and the like may be added.

To prepare suppositories, for example, the composition of the present invention can be molded by per se known methods into oily or aqueous solid, semisolid or liquid suppositories.

The pharmaceutical composition of the present invention has low toxicity and exhibits potent pharmacological properties such as therapeutic properties and preventative or inhibitive properties against diseases associated with angiogenesis, for example, inflammatory diseases (e.g., rheumatoid arthritis, etc.), diabetogenous retinopathy, tumors such as malignant tumors (e.g., cancer such as mastocarcinoma, hepatoma, colic carcinoma, Kaposi's sarcoma, etc.). It is therefore useful as drugs for mammals (e.g., mouse, rat, monkey, cattle, dog, human, etc.) such as agents for treating or preventing diseases associated with angiogenesis, for example, inflammatory diseases (e.g., rheumatoid arthritis, etc.), diabetogenous retinopathy, tumor (e.g., cancer such as mastocarcinoma, hepatoma, colic carcinoma, Kaposi's sarcoma, etc.). For example, in the case of treatment of cancer by administering the composition subcutaneously, intramuscularly or the like, the pharmacological activities of the fumagillol can be obtained over a long period of time by the sustained-release effect of the composition of the present invention. The number of administrations can therefore be reduced. The composition can also be used as a chemically obstructing agent by directly injecting the composition into a cancer-controlling artery. In the case of treatment of an adult patient having cancer, the dose of the fumagillol derivative can be appropriately selected depending upon the kind of tumor, site, size, and kind of fumagillol derivative. For example, the composition of a solution or dispersion of the fumagillol derivative of about 0.1 mg to about 5.0 g, preferably about 1.0 mg to about 2.0 g, more preferably about 50 mg to about 1.0 g in the fatty acid ester of glycerin or polyglycerin may be administered at prescribed intervals.

The administration frequency can be appropriately selected depending upon the kind of disease and dosage form. For example, nasal preparations can be administered two or three times a day, suppositories can be usually administered once a day. In the parenteral formulation, subcutaneous or intramuscular depot formulations can be injected one to three times a week. In the case of injection into the tumor-controlled artery or tumor itself, frequently repeated injections are not required and a single injection once every one to 4 weeks may be sufficient for the desired therapeutic effects.

The pharmaceutical composition of the present invention improves the stability of the fumagillol derivative, and thereby provides more potent pharmacological activities. Thus, more certain therapeutic effects can be expected.

Further, the pharmaceutical composition prevents decomposition of the fumagillol derivative during storage by stabilizing the fumagillol derivative. Still further, the composition is a sustained-release composition. Thus, the composition of the present invention can advantageously be used as a pharmaceutical preparation or the like.

The following examples further illustrate the present invention in detail but are not to be construed to limit the scope thereof.

EXAMPLE 1

6-O-(N-Chloroacetylcarbamoyl)fumagillol (hereinafter referred to as Compound A) was dissolved in Miglyol 812 (caprylic acid/capric acid triglyceride)(Huls Aktiengesellschaft, Germany), so that the concentrations of Compound A became 1 mg/ml (0.1% w/v) and 10 mg/ml (1% w/v), respectively, based on Miglyol 812 to obtain homogeneous solutions. These solutions were dispensed into vials in which the atmosphere had been replaced with nitrogen, and allowed to stand at 37° C. The ratios of remaining Compound A were determined. For comparison, Compound A was dissolved in sesame oil, Lipiodol (the main component is iodinated poppy seed oil) and water, respectively, and resulting solutions were tested likewise. The results are shown in Table 1.

TABLE 1

| | Ratio of remaining Compound A stored at 37° C. | | |
| --- | --- | --- | --- |
| | After 1 day | After 5 days | After 14 days |
| Miglyol 812 solution | | | |
| 1 mg/ml | 100.0% | 98.5% | 98.8% |
| 10 mg/ml | 99.2% | 98.1% | 100.0% |

TABLE 1-continued

|  | Ratio of remaining Compound A stored at 37° C. | | |
|---|---|---|---|
|  | After 1 day | After 5 days | After 14 days |
| Aqueous solution | | | |
| 1 mg/ml | 2.2% | 0.0% | 0.0% |
| Sesame oil solution | | | |
| 10 mg/ml | — | 96.6% | 83.8% |
| Lipiodol solution | | | |
| 1 mg/ml | 99.7% | 95.2% | 75.7% |
| 10 mg/ml | 101.0% | 96.0% | 89.0% |

Compound A in the fatty acid triglyceride, i.e., Miglyol 812, decomposed little even after 14 days and was far more stable than that in the aqueous solution and the other oily solutions.

From the excellent stability of this preparation including Miglyol 812, it is presumed that decomposition by hydrolysis and oxidation was prevented by the scarce water content and the triglyceride composition with the saturated fatty acids.

EXAMPLE 2

Compound A was dissolved in Miglyol 812 so that the concentration of Compound A became 10 mg/ml (1% w/v) based on Myglyol 812 to prepare a homogeneous solution. This solution was dispensed into vials in which the atmosphere had been replaced with nitrogen. The vials were allowed to stand at 25° C., 40° C. and 60° C., respectively. The ratios of remaining Compound A were determined after 1 month and 2 months. Similar experiments were performed using Lipiodol. The results are shown in Table 2.

TABLE 2

|  | 25° C. | 40° C. | 60° C. |
|---|---|---|---|
|  | Ratio of remaining Compound A after 1 month | | |
| Miglyol 812 solution | 100.3% | 98.5% | 89.6% |
| Lipiodol solution | 95.8% | 73.6% | 1.1% |
|  | Ratio of remaining Compound A after 2 month | | |
| Miglyol 812 solution | 98.8% | 96.2% | 80.0% |
| Lipiodol solution | 93.5% | 56.9% | 0.2% |

Compound A was far more stable when Miglyol 812 was used than when Lipiodol was used.

EXAMPLE 3

To test the ratio of remaining Compound A in blood or fluid, 1/30 M phosphate buffer (pH 7.0, each 5 ml) was added to each (1 ml) of the solutions used in Example 1. The mixture was stirred at a speed of 10 rpm with a rotator. The content of Compound A in the oil phase was determined over time (i.e., after 1 day, 2 days and 7 days at 37° C.) to calculate the ratios of remaining Compound A. The results are shown in Table 3.

TABLE 3

|  | Ratio of remaining Compound A | | |
|---|---|---|---|
|  | After 1 day | After 2 days | After 7 days |
| Miglyol 812 solution | | | |
| 1 mg/ml | 57.8% | 44.1% | 2.8% |
| 10 mg/ml | 61.8% | 50.2% | 10.7% |
| Sesame oil solution | | | |
| 10 mg/ml | 22.4% | 15.3% | 0.0% |
| Lipiodol solution | | | |
| 1 mg/ml | 39.3% | 25.6% | 2.5% |
| 10 mg/ml | 53.1% | 28.3% | 5.2% |

Compound A was most stable when the fatty acid triglyceride was used in comparison with the case wherein the other oily solutions were used, and it was found that the drug was sustained-released over at least 7 days.

EXAMPLE 4

Dynasan 118 (stearic acid triglyceride, Huls)(5 g) was melted by warming it to about 90° C. Then Compound A was added so that the concentrations of Compound A became 2% (about 2% w/v) and 10% (about 10% w/v) based on Dynasan 118, respectively, and dissolved. These solutions were subjected to a spray chilling method to give global microparticles (3 g per solution) with a particle diameter of 125 to 250 μm (hereinafter referred to as TG18-msp(2%) and TG18-msp(10%), respectively). Likewise, Dynasan 114 (myristic acid triglyceride, Huls)(5 g) was melted by warming it to about 60° C. Compound A was added so that the concentrations of Compound A became 2% (about 2% w/v) and 10% (about 10% w/v) based on Dynasan 114, respectively, and dissolved. These solutions were subjected to the spray chilling method to give global microparticles (3 g per solution) with a particle diameter of 125 to 250 μm (these solutions are hereinafter referred to as TG14-msp(2%) and TG14-msp(10%), respectively).

EXAMPLE 5

According to the same manner as that described in Example 1, TG14-msp(2%), TG14-msp(10%), TG18-msp(2%) and TG18-msp(10%) obtained in Example 4 were allowed to stand at 37° C. in vials in which the atmosphere had been replaced with nitrogen, and the ratios of remaining Compound A were determined. The results are shown in Table 4.

TABLE 4

|  | Ratio of remaining Compound A stored at 37° C. | |
|---|---|---|
|  | After 5 days | After 14 days |
| TG14-msp (2%) | 102.3% | 93.2% |
| TG14-msp (10%) | 96.7% | 100.6% |
| TG18-msp (2%) | 97.5% | 90.8% |
| TG18-msp (10%) | 97.5% | 98.1% |

Compound A was more stable when the fatty acid triglyceride was used than when sesame oil, Lipiodol or water as shown in Table 1 was used. Particularly in TG14-msp(10%) and TG18-msp(10%), Compound A decomposed little, if at all, and was extremely stable even after 14 days.

EXAMPLE 6

According to the same manner as that described in Example 3, 1/30M phosphate buffer (pH 7.0, each 5 ml) was added to TG18-msp(2%) and TG18-msp(10%) (each about 10 mg) obtained in Example 4. The mixture was stirred at a rate of 10 rpm with a rotator. Then TG18-msp (2%) and TG18-msp (10%) were sampled over time. The contents of Compound A in the particles were determined to calculate the ratios of remaining Compound A. The results are shown in Table 5.

TABLE 5

|  | Ratio of remaining Compound A | | | |
|---|---|---|---|---|
|  | After 1 day | After 3 days | After 7 days | After 14 days |
| TG18-msp (2%) | 101.0% | 91.1% | 85.5% | 72.0% |
| TG18-msp (10%) | 83.6% | 63.5% | 32.4% | 13.8% |

The rate of release of Compound A was slightly high in TG18-msp(10%), but it is apparent that the sustained-release over at least 14 days was obtained in both TG-msp(2%) and TG18-msp(10%).

EXAMPLE 7

Poem J46B (Tetraglycerin hexabehenate; Riken Vitamin, Japan)(3 g) was melted by warming it to about 90° C. Compound A was added to so that the concentration of Compound A became 10% by weight (about 10% w/v) based on above Poem J46B, and dissolved. Then this solution was solidified to give cylindrical pellets (3 g) with a diameter of 2 mm (hereinafter referred to as Poem J46B-pellet).

The Poem J46B-pellet thus obtained was allowed to stand at 37° C. in vials in which the atmosphere had been replaced with nitrogen, and the ratio of remaining Compound A was determined. The results are shown in Table 6.

TABLE 6

|  | Ratio of remaining Compound A stored at 37° C. | | |
|---|---|---|---|
|  | After 1 day | After 5 days | After 14 days |
| Poem J46B-pellet | 102.0% | 97.6% | 76.6% |

Compound A was extremely stable when the polyglycerin fatty acid ester was used in comparison with the case wherein the aqueous solution was used as shown in Table 1.

EXAMPLE 8

Compound A was dissolved in Decaglyn 10-O (decaglycerin decaoleate; Nikko Chemicals, Japan) so that the concentration of Compound A became 10 mg/ml based on Decaglyn 10) such that a homogeneous solution was obtained.

According to the same manner as that described in Example 3, 1/30M phosphate buffer (pH 7.0)(each 5 ml) was added to the Poem J46B-pellet (about 10 mg) obtained in Example 7 and the above Decaglyn 10-0 solution (1 ml). The mixture was stirred at a rate of 10 rpm with a rotator. Then the contents of Compound A in the Poem J46B-pellet and Decaglyn 10-O solution were determined over time to calculate the ratios of remaining Compound A. The results are shown in Table 7.

TABLE 7

|  | Ratio of remaining Compound A | | | |
|---|---|---|---|---|
|  | After 1 day | After 2 days | After 7 days | After 14 days |
| Poem J46B-pellet | 96.7% | 94.8% | 78.5% | 58.8% |
| Decaglyn 10-O solution | 52.4% | 32.5% | 3.5% | 0.0% |

In the case of using the tetraglycerin hexabehenate wherein the fatty acid in the fatty acid ester of glycerin was saturated, Compound A was more stable than, and the sustained-release was superior to, the case of using decaglycerin decaoleate which has unsaturated fatty acids.

EXAMPLE 9

Cancer-bearing rabbits were prepared by transplanting cellular fluid of $VX_2$ carcinoma subcutaneously into the lower part of the knee of right hind legs of male Kbs:JW rabbits. Two weeks after the transplantation, the rabbits were divided into 4 groups. An aqueous solution (1 ml) containing Compound A (1 mg), a solution of Compound A (1 mg) in Miglyol 812 (0.5 ml) and a solution of Compound A (5 mg) in Miglyol 812 (0.5 ml) were administered to the groups, respectively, from the upper stream of the arteriae femoralis on the same side. The volumes of the tumors were measured 5 days after administration. The relative ratios (V5/V0)(the volume of each group before administration is considered to be 100%) and the ratios (T/C) by volume based on the untreated control groups were calculated. The results are shown in Table 8.

TABLE 8

|  | Number of examples | V5/V0 | T/C |
|---|---|---|---|
| Miglyol 812 solution |  |  |  |
| 1 mg administered group | 3 | 89% | 37% |
| 5 mg administered group | 6 | 75% | 32% |
| Aqueous solution |  |  |  |
| 1 mg administered group | 3 | 175% | 74% |
| Untreated (control) group | 21 | 238% | 100% |

In the group to which an aqueous solution containing Compound A (1 mg) was administered, tumor volume was 74% of the untreated group and 175% of such before administration. On the other hand, in the groups to which 1 mg and 5 mg of Compound A in Miglyol 812 was administered intra-arterially, tumor volume was reduced to 37% and 32%, respectively, of the untreated group, and to 89% and 75%, respectively, of such before the administration.

EXAMPLE 10

Cancer-bearing rabbits similar to those of Example 9 were divided into 3 groups two weeks after transplantation. TG18-msp(2%), TG18-msp(10%), TG14-msp(2%) and TG14-msp(10%) (each 50 mg; each 1 mg and 5 mg in terms of Compound A) prepared in Example 4 were administered to the groups, respectively, from the upper stream of the arteriae femoralis on the same side. The volumes of the tumors were measured 5 days after administration. The relative ratios (V5/V0)(the volume of each group before administration is considered to be 100%) and the ratio (T/C) by volume based on the untreated control group were calculated. The results are shown in Table 9.

TABLE 9

|  | Number of examples | V5/V0 | T/C |
|---|---|---|---|
| TG18-msp (2%) administered group | 3 | 65% | 27% |
| TG18-msp (10%) administered group | 3 | 49% | 21% |
| TG14-msp (2%) administered group | 3 | 63% | 26% |
| TG14-msp (10%) administered group | 2 | 65% | 27% |
| Untreated (control) group | 21 | 238% | 100% |

In the group to which TG18-msp(2%) and TG18-msp(10%) were administered intra-arterially, tumor volume was reduced to 27% and 21%, respectively, of the untreated group and reduced to 65% and 49%, respectively, of such before administration. In the groups to which TG14-msp(2%) and TG14-msp(10%) were administered intra-arterially, tumor volume was reduced to 26% and 27%, respectively, of the untreated group, and to 63% and 65%, respectively, of such before administration. Extremely potent tumor-growth inhibitory activity was observed in comparison with the results of the aqueous solution administered group shown in Table 8.

EXAMPLE 11

6-O-(N-Chloroacetylcarbamoyl)fumagillol (Compound A)(50 g) and chlorobutanol (30 g) were dissolved in Miglyol 812 (see, Example 1)(1 liter). The solution was filtered with Millipore filter (Millex-FG, 0.2 μm) to remove microorganisms. The oily solution (each 2 ml) was packed into an ampoule, and the atmosphere in the ampoule was replace with nitrogen. The ampoule was melt-sealed, and then sterilized at 121° C for 20 minutes with an autoclave to obtain a preparation for injection (containing 0.1 g of Compound A).

EXAMPLE 12

Dynasan 118 (see, Example 4)(920 g) was melted by warming it to about 90° C. 6-O-(N-Chloroacetylcarbamoyl)fumagillol (Compound A)(50 g) and chlorobutanol (30 g) were dissolved in the liquid Dynasan 118. The resulting solution was subjected to spray drying by using a spray dryer (Mobile Minors Spray Dryer, manufactured by Nitroatomizer) with a nozzle temperature of 90° to 100° C. The resulting powder with a particle diameter of 50 to 200 μm was separated with a sieve. Mannitol (100 g) was mixed well with 500 g of the powder. Then this 600 mg mixture was packed into a vial for use as an injectable preparation to be suspended just before the use. As the dispersive medium, 1% carboxymethylcellulose sodium salt or 0.5% Tween 80 aqueous solution was used in an amount of 2 ml per vial.

EXAMPLE 13

4-(N'-chloroacetylureido)-2-(1,2-epoxy-1,5-dimethyl-4-hexenyl)-1-(1,3-dihydrobenzo[c]thiophen-2-ylio)-methyl-3-methoxycyclohexanol chloride (hereinafter referred to as Compound B) was dispersed in Miglyol 812 containing 2% w/v Tween 80 by using a sonicator (Sono Cleaner, manufactured by Kaijo Denki) so that the concentration of Compound B became 1 mg/ml (0.1% w/v) based on Miglyol 812 containing Tween 80 such that a homogeneous suspension was obtained.

What is claimed is:

1. A pharmaceutical composition comprising a fumagillol derivative represented by the formula (I):

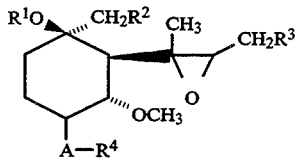

wherein $R^1$ is hydrogen; $R^2$ is halogen, $N(O)_m R^5 R^6$, $N^+ R^5 R^6 R^7 \cdot X^-$, $S(O)_n R^5$ or $S^+ R^5 R^6 \cdot X^-$, in which $R^5$, $R^6$ and $R^7$ represent each independently a substituted or unsubstituted hydrocarbon group or a substituted or unsubstituted heterocyclic group; $X^-$ represents a counter anion; m represents 0 or 1; n represents an integer of 0 to 2; or $R^5$ and $R^6$ together with the adjacent nitrogen or sulfur atom may form a nitrogen- or sulfur-containing heterocyclic group which is substituted or unsubstituted and may form a condensed ring; or $R^1$ and $R^2$ together are a chemical bond; $R^3$ is a substituted or unsubstituted 2-methyl-1-propenyl group or a substituted or unsubstituted isobutyl group; A is O or $NR^8$, in which $R^8$ represents hydrogen, a substituted or unsubstituted lower alkyl group or a substituted or unsubstituted aryl group; and $R^4$ is hydrogen, a substituted or unsubstituted hydrocarbon group or a substituted or unsubstituted acyl group; or a salt thereof, and a fatty acid ester of glycerin or polyglycerin wherein the fatty acid constituting the fatty acid ester is a saturated fatty acid having 6 to 22 carbon atoms.

2. A pharmaceutical composition according to claim 1, wherein the fumagillol derivative is dissolved or dispersed in the fatty acid ester of glycerin or polyglycerin.

3. A pharmaceutical composition according to claim 1, wherein the fatty acid ester of glycerin is a fatty acid triglyceride.

4. A pharmaceutical composition according to claim 1, wherein the fumagillol derivative is dissolved in a fatty acid triglyceride.

5. A pharmaceutical composition according to claim 1, wherein the ratio of the fumagillol derivative based on the fatty acid ester of glycerin, or polyglycerin is about 0.001 to about 50% (w/v).

6. A pharmaceutical composition according to claim 1, wherein the degree of esterification of the glycerin or polyglycerin is at least about 60%.

7. A pharmaceutical composition according to claim 1, wherein the degree of polymerization of the polyglycerin is 2 to 10.

8. A pharmaceutical composition according to claim 1, which comprises an injectable composition.

9. A pharmaceutical composition according to claim 1, which is in a liquid form.

10. A pharmaceutical composition according to claim 1, which comprises a solid micro-particle composition having an particle diameter of about 10 to 1000 μm.

11. A pharmaceutical composition according to claim 1 wherein $R^1$ and $R^2$ together are a chemical bond, or $R^1$ is hydrogen and $R^2$ is $N(O)_m R^5 R^6$, $N^+ R^5 R^6 R^7 \cdot X^-, S(O)_n R^5$ or $S^+ R^5 R^6 \cdot X^-$; A is O or NH; $R^3$ is a substituted or unsubstituted 2-methyl-1-propenyl or isobutyl group; and $R^4$ is hydrogen or a substituted or unsubstituted carbamoyl group.

12. A pharmaceutical composition according to claim 1, wherein $R^1$ and $R^2$ together are a chemical bond.

13. A pharmaceutical composition according to claim 11, wherein A is O; $R^3$ is a 2-methyl-1-propenyl or isobutyl group which is unsubstituted or substituted with a hydroxyl or dialkylamino group; $R^4$ is a carbamoyl group which is substituted with a $C_{1-6}$ alkyl or halogeno-$C_{1-6}$ alkanoyl group.

14. A pharmaceutical composition according to claim 1, wherein the fumagillol derivative is 6-O-(N-chloroacetylcarbamoyl)fumagillol.

15. A pharmaceutical composition according to claim 1, wherein the fumagillol derivative is 4-(N'-chloroacetylureido)-2-(1,2-epoxy-1,5-dimethyl-4-hexenyl )-1-(1,3-dihydrobenzo[c]thiophen-2-ylio)methyl-3-methoxycyclohexanol chloride.

16. A pharmaceutical composition according to claim 1, wherein the main component of the fatty acid which constitutes the fatty acid ester is caprylic acid ($C_8$).

17. A pharmaceutical composition according to claim 1, wherein the main component of the fatty acid which constitutes the fatty acid ester is capric acid ($C_{10}$).

18. A pharmaceutical composition according to claim 1, wherein the main component of the fatty acid which constitutes the fatty acid ester is caprylic acid ($C_8$) and capric acid ($C_{10}$).

19. A pharmaceutical composition according to claim 1, wherein the main component of the fatty acid which constitutes the fatty acid ester is lauric acid ($C_{12}$).

20. A pharmaceutical composition according to claim 1, wherein the main component of the fatty acid which constitutes the fatty acid ester is myristic acid ($C_{14}$).

21. A pharmaceutical composition according to claim 1, wherein the main component of the fatty acid which constitutes the fatty acid ester is palmitic acid ($C_{16}$).

22. A pharmaceutical composition according to claim 1, wherein the main component of the fatty acid which constitutes the fatty acid ester is stearic acid ($C_{18}$).

23. A pharmaceutical composition according to claim 1, wherein the main component of the fatty acid which constitutes the fatty acid ester is arachidic acid ($C_{20}$).

24. A pharmaceutical composition according to claim 1, wherein the main component of the fatty acid which constitutes the fatty acid ester is behenic acid ($C_{22}$).

25. A pharmaceutical composition according to claim 1, which is an angiogenesis inhibitory composition.

26. A method of stabilizing a fumagillol derivative (I) or a salt thereof as defined in claim 1 which comprises dissolving or dispersing the fumagillol derivative in a fatty acid ester of glycerin or polyglycerin as defined in claim 1.

27. A method of treating a disease associated with angiogenesis in mammals which comprises administering the pharmaceutical composition according to claim 1 to a subject in need thereof.

28. A method according to claim 27, wherein the disease is a malignant tumor.

29. A method according to claim 28, wherein the malignant tumor is hepatoma.

30. A pharmaceutical composition for inhibiting angiogenesis comprising a fumagillol derivative (I) or a salt thereof as defined in claim 1 and a fatty acid ester of glycerin or polyglycerin as defined in claim 1.

31. A stable, sustained-release composition for inhibiting angiogenesis comprising a fumagillol derivative (I) or a salt thereof as defined in claim 1 and a fatty acid ester of glycerin or polyglycerin as defined in claim 1.

* * * * *